US00PP14900P3

(12) United States Plant Patent
Kordes

(10) Patent No.: US PP14,900 P3
(45) Date of Patent: Jun. 15, 2004

(54) HYBRID TEA ROSE PLANT NAMED 'KORTUREK'

(50) Latin Name: *Hybrid Tea Rose*
Varietal Denomination: KORturek

(75) Inventor: Tim-Hermann Kordes, Offenseth-Sparrieshoop (DE)

(73) Assignee: W. Kordes Sohne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 55 days.

(21) Appl. No.: 10/100,425

(22) Filed: Mar. 18, 2002

(65) Prior Publication Data

US 2003/0177550 P1 Sep. 18, 2003

(51) Int. Cl.[7] ..... A01H 5/00

(52) U.S. Cl. ..... Plt./133

(58) Field of Search ..... Plt./133, 130

*Primary Examiner*—Howard J. Locker
(74) *Attorney, Agent, or Firm*—Webb Ziesenheim Logsdon Orkin & Hanson, P.C.

(57) ABSTRACT

This invention relates to a new and distinct variety of hybrid tea rose plant named 'KORturek' which has attractive white colored flowers and attractive dark green and glossy foliage. This new variety is characterized by having large and well turbinated buds, a high production of long stems with a long vase life, vigorous and upright growth and good tolerance to powdery mildew. The variety successfully propagates from softwood cuttings and is well suitable for year round production of cut flowers in commercial glass houses as a flowering cut rose.

2 Drawing Sheets

Varietal denomination: 'KORturek'.

BACKGROUND OF THE INVENTION

The present invention constitutes a new and distinct variety of hybrid tea rose plant named 'KORturek'. The new variety originated as a single plant as a result of artifically pollinating 'KORmodika' (not patented) with an unnamed seedling (not patented) in a cultivated greenhouse environment in 2000 in Germany. The mutation was vegetatively propagated from cuttings by self-rooting and tested for productivity and growth. The objectives of the testing and development of this rose variety for commercial greenhouse culture was to create a new and distinct variety with:

1. Uniform, large buds that are well turbinated and flowers with good vase-life.
2. Novel flower color.
3. High cut flower production, with medium to long stems.
4. Vigorous, upright growth.
5. Suitability for production from softwood cuttings.
6. Good tolerance to powdery mildew.
7. Suitability for production of cut flowers under greenhouse growing conditions.

This combination of qualities was not present in previously available commercial cultivars of this type and distinguish 'KORturek' from other varieties known to the inventor.

The seeds from hybridization were planted in a controlled environment and evaluations were conducted on the resulting plants. 'KORturek' was selected in a development program in Klein Offenseth, Sparrieshoop, Germany.

Asexual reproduction of 'KORturek' by cuttings was first done on May 15, 2001 in Germany and later in California.

The reproductions by cuttings done in controlled greenhouse environments have confirmed that distinguishing features of the new cultivar come true, remain stable and are retained through successive propagations. 'KORturek' is a highly productive hybrid tea rose with a vase life greater than 11 days. Under conventional greenhouse conditions in Germany (64° C. nights, 26° C. days), 'KORturek' produces 220 stems per plant per square meter per year averaging 65 cm long.

The new rose is distinguished from 'KORcilmo' by the following combinations of characteristics:

| | KORturek | KORcilmo |
|---|---|---|
| Petal color, upper surface | 155A–B | 158D |
| Petal color, reverse surface | 155A–B | 158D |
| Petal count | 35–40 | 30–35 |

DESCRIPTION OF THE DRAWINGS

The accompanying color illustrations show as true as possible in color photographs of this type, the typical characteristics of the buds, flowers, leaves, stems of 'KORturek'. Specifically illustrated as follows.

In photo sheet #1.

DESCRIPTION OF THE PLANT

Figures 1, 2, 3, 4, 5, 6, 7, 8, 9:
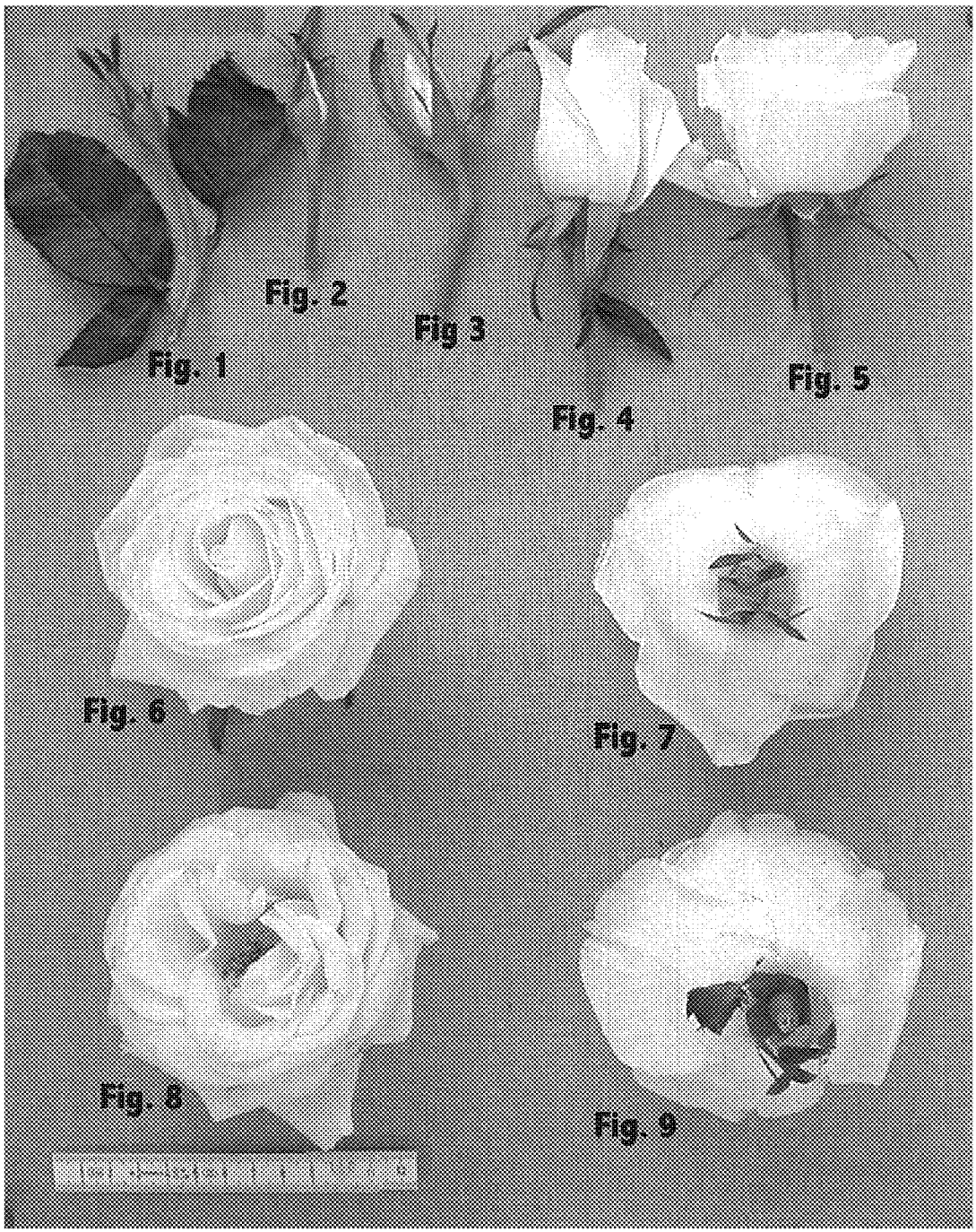
FIG. 1 illustrates a young shoot.
FIG. 2 illustrates a bud before opening of the sepals.
FIG. 3 illustrates a bud at the opening of the sepals.
FIG. 4 illustrates a bud at the opening of the petals.
FIG. 5 illustrates a flower during course of opening.
FIG. 6 illustrates an open flower, plan obverse view.
FIG. 7 illustrates an open flower, plan reverse view.
FIG. 8 illustrates a fully open flower, plan obverse view.
FIG. 9 illustrates a fully open flower, plan reverse view. In photo sheet #2.
Figures 10, 11, 12, 13, 14, 15, 16, 17, 18:
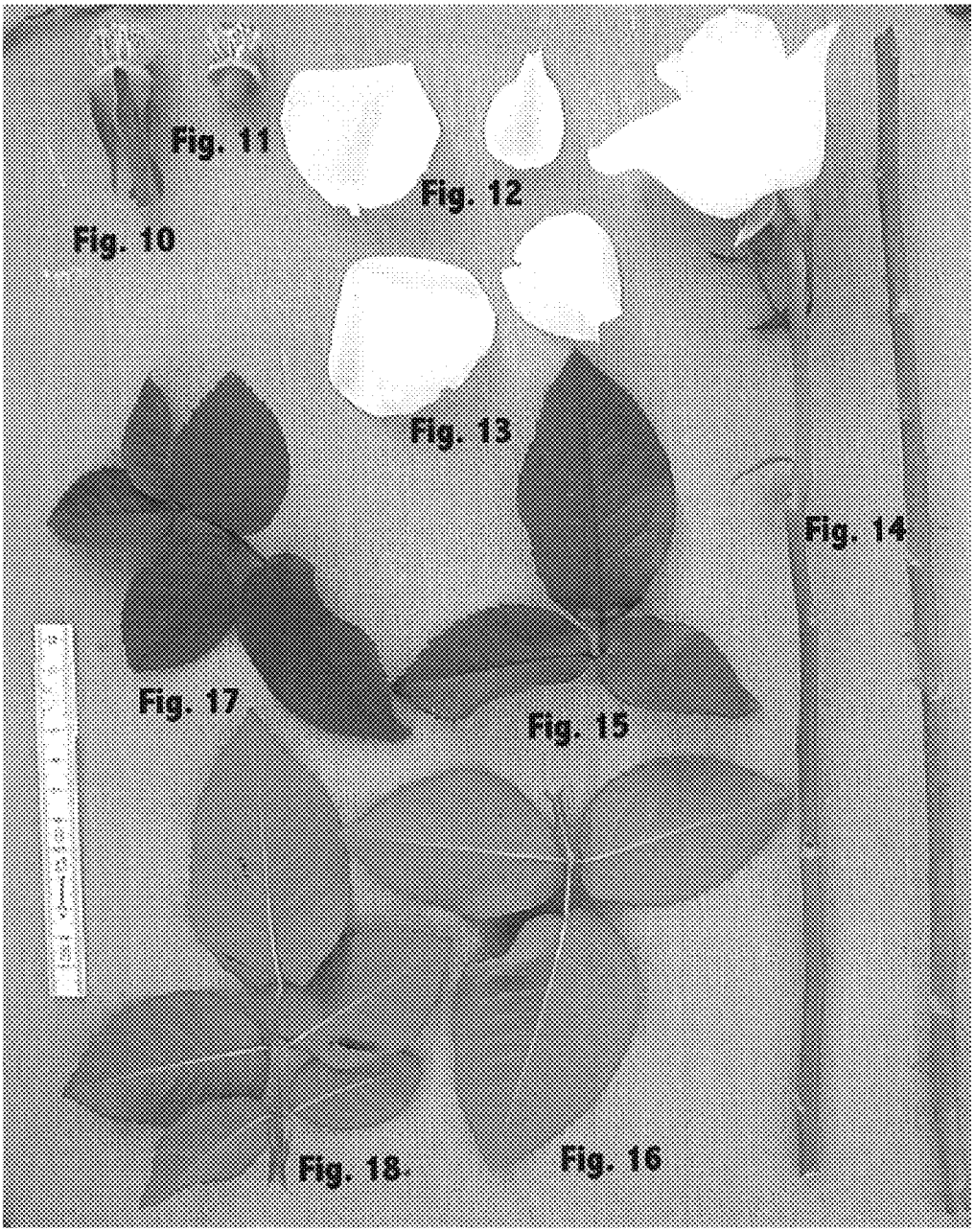
FIG. 10 illustrates a receptacle showing stamens and pistils.
FIG. 11 illustrates a receptacle showing pistils (stamens removed)
FIG. 12 illustrates flower petals detached, outer surface.
FIG. 13 illustrates flower petals detached, inner surface.
FIG. 14 illustrates a bare stem exhibiting thorns and flower attachment.
FIG. 15 illustrates 3 leaflets, upper side.
FIG. 16 illustrates 3 leaflets, under side.
FIG. 17 illustrates 5 leaflets, upper side.
FIG. 18 illustrates 5 leaflets, under side.

The following is a detailed description of 'KORturek', as observed in its growth in greenhouses in Klein Offenseth-Sparrieshoop, Germany, and glass houses in California. The age of the observed plant was 11 to 13 months after propagation, produced as a cut rose plant. The cultivation at both locations was based on 18–26° C. temperatures. Color references are made using The Royal Horticultural Society (London, England) Colour Chart, 1995, except where common terms of color are used. For a comparison, the nearest existing rose variety is 'JACcream', U.S. Plant Pat. No. 9,328.

Table 1 details several physical characteristics of 'KORturek' and 'JACcream'.

TABLE 1

| | 'KORturek' | 'JACcream' |
|---|---|---|
| Petal color, upper surface | 155A–B | 155B |
| Petal color, reverse surface | 155A–B | 155B |
| Petal count | 35–40 | 30–35 |

THE PLANT

Classification:
- *Botanical.*—*Rosa hybrida.*
- *Commercial.*—Hybrid tea rose.

Growth habit: Very vigorous. Grows strong upright to bushy. Production time for floral stems is generally 6 to 8 weeks depending on average temperature, light level, and cultural practices.

Height: Plants which were pruned at a height of 0.5 meters, produced floral stems averaging 65 cm. in length.

Stem:
- *Color.*—Young wood: 138C with intonations of 184B. Older wood: 138B.

Thorns:
- *Incidence.*—Average number of thorns on both main branches and lowering stems is 15–20.
- *Size.*—7–10 mm.
- *Color.*—At base 138C with intonations of 172B at tip.
- *Shape.*—Deep concave.

Surface:
- *Young wood.*—Smooth.
- *Older wood.*—Smooth.
- *Stem diameter.*—5–7 mm.
- *Internode length.*—50–70 mm.
- *Number of internodes.*—15–16.

FOLIAGE

Arrangement: Alternate, compound with 3, 5, or 7 leaflets per leaf, generally symmetrical, abundant, and flat in aspect. Stipules at petiole base.

Quantity of leaves: 15–16 per lateral branch.

Leaf size (3, 5, or 7 leaflet leaf):
- *Length.*—70–140 mm.
- *Width.*—80–110 mm.

Petioles:
- *Color.*—139C with intonations of 183B.
- *Margin.*—Entire, with stipitate glands.
- *Length.*—15–20 mm.
- *Diameter.*—About 1–2 mm.

Stipules:
- *Size.*—15–20 mm.
- *Surface.*—Smooth.
- *Color.*—Between 139C and 139D.
- *Margin.*—Entire, with stipitate glands.

Rachis:
- *Color.*—139C with intonations of 183B.
- *Margin.*—Margin with stipitate glands.
- *Length.*—50–65 mm.

Leaflets:
- *Edge.*—Serrated.
- *Serration.*—Single.
- *Shape.*—Ovate with acute apex and obtuse base.
- *Texture.*—Smooth.
- *Appearance.*—Glossy.
- *Size.*—Length: 40–75 mm. Width: 25–45 mm.
- *Color.*—Young foliage: Upper surface: 144A with intonations of 183B. Lower surface: 144B with intonations of 183B. Mature foliage: Upper surface: 137A, edge 183B. Lower surface: 139B, edge 183B.

BUD

Size upon opening:
- *Height.*—40–45 mm.
- *Width.*—25–30 mm.

Shape: Long, pointed ovoid.

Color at one-quarter open: 155A–155B.

FLOWERS

Flowering characteristics: Recurrent, generally 1 bud per flowering stem.

Duration: On the plant, flowers last 15–17 days. When cut and placed in a vase, flowers last 11–12 days.

Fragrance: Light.

Size: 90–100 mm in diameter.

Form when viewed from side:
- *Upon opening.*—Cupped.
- *Open flower.*—Cupped.

Peduncle:
- *Color.*—143A.
- *Texture.*—Smooth, with pubescence and prickles.
- *Length.*—50–75 mm.
- *Strength.*—Upright.

Receptacle:
- *Surface.*—Smooth, glabrous.
- *Shape.*—Funnel-shaped.
- *Size.*—Height: 8–10 mm. Width: 8–10 mm.
- *Color.*—143A.

Sepals:
- *Quantity.*—5.
- *Shape.*—Narrowly ovate with acute tip.
- *Texture.*—Leathery.

*Margin.*—Foliaceous appendages on 2 of the 5 sepals.
*Appearance.*—Dull.
*Color.*—Upper surface: 138A with intonations of 64A. Reverse surface: 139C.

Petals:
*Color.*—Upon opening: Upper surface: Between 155A and 155B. Reverse surface: Between 155A and 155B. After opening: Upper surface: Between 155A and 155B. Reverse surface: Between 155A and 155B.
*General tonality on open flower.*—Between 155A and 155B on third day, Between 155A and 155B afterwards.
*Basal petal spots.*—None.

Petals:
*Reflex.*—Outermost petals reflex backwards at opening. When fully open all petals reflex backwards.
*Texture.*—Smooth.
*Petal edge.*—Uniform.
*Petal count.*—Approximately 35–40 on average per flower.
*Petal size.*—Length: 50 mm. Width: 50 mm.
*Shape.*—Outer petals: Round. Inner petals: Ovate.

Petaloids: Commonly none.

REPRODUCTIVE ORGANS

Stamen: Approximately 140–150 on average per flower.
*Pollen.*—Color: 22A. Abundance: Average.
*Anthers.*—Size: 4–5 mm. Color: 22A. Shape: Oblong.
*Filaments.*—Size: 8–10 mm. Color: 155B with intonations of 66A towards the anther attachment.

Pistils: Approximately 120–130 on average per flower.
*Stigmas.*—Location: Below anthers. Color: 155C.
*Styles.*—Color: 66A. Length: 3–5 mm.

Aptitude to bear fruit: Poor.

Resistance to diseases: Above average resistance to mildew and Botrytis under normal growing conditions in Klein Offenseth-Sparrieshoop, Germany and California.

Productivity: Commonly produces approximately 210 to 230 flowers/$m^2$ year under greenhouse conditions.

Hips/seeds: Unknown, the plant has not been grown to the stage of seed development due to the fact that the variety is developed for use as a flowering cut-rose only.

Winter hardiness and drought/heat tolerance: Due to the fact, that this variety is a flowering cut-rose plant, developed for greenhouse cultivation only, the plant has not been tested for winter hardiness or drought/heat tolerance.

I claim:

1. The new and distinct variety of hybrid tea rose plant named ‘KORturek’ as described and illustrated.

* * * * *

UNITED STATES PATENT AND TRADEMARK OFFICE

CERTIFICATE OF CORRECTION

PATENT NO. : PP 14,900 P3
APPLICATION NO. : 10/100425
DATED : June 15, 2004
INVENTOR(S) : Tim-Hermann Kordes It is certified that error appears in the above-identified patent and that said Letters Patent is hereby corrected as shown below:

Face of patent,
See Item (50) Latin Name: "Hybrid Tea Rose" should read --Rosa Hybrida--

Face of patent,
Column 1, under "BACKGROUND OF THE INVENTION", Line 10, "The mutation" should read --The plant--

Column 3, under "THE PLANT", Thorns:, Line 15, "lowering stems" should read --flowering stems--

Signed and Sealed this

Fourth Day of September, 2007

JON W. DUDAS
*Director of the United States Patent and Trademark Office*